(12) United States Patent
Dietrich et al.

(10) Patent No.: US 7,147,869 B2
(45) Date of Patent: Dec. 12, 2006

(54) RAPIDLY DISINTEGRATING TABLET COMPRISING AN ACID-LABILE ACTIVE INGREDIENT

(75) Inventors: Rango Dietrich, Constance (DE); Hartmut Ney, Constance (DE); Rudolf Linder, Constance (DE)

(73) Assignee: Altana Pharma AG, Constance (DE)

( * ) Notice: Subject to any disclaimer, the term of this patent is extended or adjusted under 35 U.S.C. 154(b) by 478 days.

(21) Appl. No.: 10/433,397

(22) PCT Filed: Dec. 6, 2001

(86) PCT No.: PCT/EP01/14340

§ 371 (c)(1),
(2), (4) Date: Jun. 3, 2003

(87) PCT Pub. No.: WO02/45694

PCT Pub. Date: Jun. 13, 2002

(65) Prior Publication Data

US 2004/0110661 A1    Jun. 10, 2004

(30) Foreign Application Priority Data

Dec. 7, 2000    (EP) ............................ 00126807

(51) Int. Cl.
*A61K 9/46* (2006.01)
(52) U.S. Cl. ........................ 424/466; 424/464
(58) Field of Classification Search ............. None
See application file for complete search history.

(56) References Cited

U.S. PATENT DOCUMENTS 3,065,142 A    11/1962    Antonides
4,006,227 A *  2/1977    Gallegos et al. ............ 424/764
6,475,510 B1 * 11/2002   Venkatesh et al. .......... 424/441

FOREIGN PATENT DOCUMENTS

| | | |
|---|---|---|
| EP | 0 005 129 | 10/1979 |
| EP | 0 174 726 | 3/1986 |
| EP | 0 244 380 | 11/1987 |
| EP | 0 268 956 | 6/1988 |
| WO | WO 92/21328 | 12/1992 |
| WO | WO 96/01623 | 1/1996 |
| WO | WO 96/01624 | 1/1996 |
| WO | WO 96/01625 | 1/1996 |
| WO | WO 97/25030 | 7/1997 |
| WO | WO 00/74654 | 12/2000 |
| WO | WO0074654 A1 * | 12/2000 |

* cited by examiner

Primary Examiner—Gollamudi S. Kishore
Assistant Examiner—Pili A. Hawes
(74) Attorney, Agent, or Firm—Nath & Associates PLLC; Joshua B. Goldberg; Sheldon M. McGee

(57) ABSTRACT

A rapidly disintegrating tablet for oral administration of acid-labile active ingredients is described. The rapidly disintegrating tablet for oral administration of an acid-labile active ingredient comprises a plurality of individual active ingredient units together with pharmaceutical excipients, where the acid-labile active ingredient is present in the individual active ingredient units in a matrix composed of a mixture comprising at least one solid paraffin and one or more substances from the group of fatty alcohol, triglyceride and fatty acid ester, and where excipients which, on oral intake of the tablet, bring about rapid disintegration of the tablet are present.

14 Claims, No Drawings

RAPIDLY DISINTEGRATING TABLET COMPRISING AN ACID-LABILE ACTIVE INGREDIENT

TECHNICAL FIELD

The present invention relates to the field of pharmaceutical technology and describes a rapidly disintegrating tablet comprising an acid-labile active ingredient, in particular an acid-labile proton pump inhibitor. The invention also relates to processes for producing the tablet.

BACKGROUND ART

It is generally known to coat oral dosage forms, e.g. tablets or pellets, which comprise an acid-labile active ingredient, with an enteric coating which, after passing through the stomach, rapidly dissolves in the alkaline medium in the intestine. One example of such acid-labile active ingredients comprises acid-labile proton pump inhibitors ($H^+/K^+$-ATPase inhibitors), in particular pyridin-2-ylmethylsulfinyl-1H-benzimidazoles like those disclosed, for example, in EP-A-0 005 129, EP-A-0 166 287, EP-A-0 174 726 and EP-A-0 268 956. Because of their $H^+/K^+$-ATPase-inhibiting effect, they are important in the therapy of disorders originating from increased gastric acid secretion. Examples of active ingredients from this group which are already commercially available are 5-methoxy-2-[(4-methoxy-3,5-dimethyl-2-pyridinyl)methylsulfinyl]-1H-benzimidazole (INN: omeprazole), 5-difluoromethoxy-2-[(3,4-dimethoxy-2-pyridinyl)methylsulfinyl]-1H-benzimidazole (INN: pantoprazole), 2-[3-methyl-4-(2,2,2-trifluoroethoxy)-2-pyridinyl)methylsulfinyl]-1H-benzimidazole (INN: lansoprazole) and 2-{[4-(3-methoxypropoxy)-3-methylpyridin-2-yl]methylsulfinyl}-1H-benzimidazole (INN: rabeprazole).

Because of their great tendency to decompose in a neutral and, in particular, acidic environment, with production also of highly colored decomposition products, it is also necessary in this case for oral preparations to protect active ingredients from the effect of acids. With the very acid-labile pyridin-2-ylmethylsulfinyl-1H-benzimidazoles it is additionally necessary for them to be processed in the tablet core or in pellets in the form of their alkaline salts, for example as sodium salts, or together with alkaline substances. Since substances suitable for enteric coatings are those with free carboxyl groups, the problem arises that the enteric coating is, because of the alkaline medium in the interior, partially or even completely dissolved from inside, and the free carboxyl groups promote decomposition of the active ingredient. It is therefore necessary to provide a sealing intermediate layer (subcoating) between the enteric coating and the alkaline tablet core or pellet. EP-A-0 244 380 proposes that cores which contain the active ingredient together with alkaline compounds or as alkaline salt be coated with at least one layer which is soluble in water or rapidly disintegrates in water and is composed of nonacidic, inert pharmaceutically acceptable substances, before the enteric layer is applied. The intermediate layer or intermediate layers act as pH-buffering zones in which hydrogen ions diffusing in from outside are able to react with the hydroxyl ions diffusing out of the alkaline core. In order to increase the buffer capacity of the intermediate layer, it is proposed to incorporate buffer substances into the intermediate layer(s). By this process it is possible in practice to obtain reasonably stable preparations. However, relatively thick intermediate layers are required in order to avoid the unsightly discolorations which occur even with only slight decomposition. In addition, considerable effort must be invested to avoid traces of moisture during production.

WO96/01623, WO96/01624 and WO96/01625 describe a dosage form for acid-labile $H^+/K^+$-ATPase inhibitors where the active ingredient units are compressed together with tablet excipients to give a tablet. The active ingredient units consist of cores which contain the acid-labile $H^+/K^+$-APTase inhibitor together with alkaline compounds or as alkaline salt. The cores of the active ingredient units are coated with one or more layers, and at least one layer has enteric properties. The enteric layer must in this case have mechanical characteristics such that the acid resistance of the active ingredient units is not impaired on compression to tablets. WO97/25030 describes the processing of the aforementioned active ingredient units to a multiparticulate (multiple unit) effervescent tablet. In this case too it is necessary for the enteric layer to have mechanical characteristics such that the acid resistance of the active ingredient units is not impaired on compression of the active ingredient units with the other ingredients of the effervescent tablet.

EP 0 548 356 describes a rapidly disintegrating multiparticulate tablet form where the active ingredient is in the form of coated microcrystals or coated microgranules. This rapidly disintegrating tablet form is said to have the advantage that it can be taken by the patient very simply and anywhere, because it can be taken without water. In addition, this form is said to have advantages for patients who have difficulties with swallowing, such as, for example, elderly people and small children. It would be desirable to provide acid-labile active ingredients likewise in such a form. As the aforementioned background art shows, however, the production of dosage forms such as tablets for acid-labile active ingredients, in particular for acid-labile proton pump inhibitors, requires technically complicated processes because it is necessary, for example, to avoid the acid resistance of the active ingredient units being impaired on compression of the active ingredient with the tablet excipients.

DESCRIPTION OF THE INVENTION

It is an object of the present invention to provide a rapidly disintegrating dosage form for the oral administration of acid-labile active ingredients which can be produced without great technical complexity, is stable and displays good controllability of active ingredient delivery. Another object of the invention is to provide a rapidly disintegrating dosage form in which it is unnecessary to protect an acid-labile active ingredient by an enteric coating.

It has now been found, surprisingly, that this object can be achieved by a rapidly disintegrating tablet comprising a plurality of individual active ingredient units together with one or more pharmaceutical excipients, where the acid-labile active ingredient is present in the individual active ingredient units in a matrix composed of a mixture comprising at least one solid paraffin and one or more substances from the group of fatty alcohol, triglyceride and fatty acid ester, and where pharmaceutical excipients which, on oral intake of the tablet, bring about rapid disintegration of the tablet are present.

The invention therefore relates to a rapidly disintegrating tablet for oral administration of an acid-labile active ingredient comprising a plurality of individual active ingredient units together with one or more pharmaceutical excipients, where the acid-labile active ingredient is present in the individual active ingredient units in a matrix composed of a mixture comprising at least one solid paraffin and one or more substances from the group of fatty alcohol, triglyceride and fatty acid ester, and where excipients which, on oral intake of the tablet, bring about rapid disintegration of the tablet are present.

The invention further relates to a rapidly disintegrating tablet for oral administration of an acid-labile active ingredient comprising a plurality of individual active ingredient units together with one or more pharmaceutical excipients, where the acid-labile active ingredient is present in the individual active ingredient units i) in a matrix composed of a mixture comprising at least one fatty alcohol and at least one solid paraffin, ii) in a matrix composed of a mixture comprising at least one triglyceride and at least one solid paraffin or iii) in a matrix composed of a mixture comprising at least one fatty acid ester and at least one solid paraffin, and where excipients which, on oral intake of the tablet, bring about rapid disintegration of the tablet are present.

Further subject matters are evident from the claims.

The numerous individual active ingredient units (also referred to hereinafter as preparations) for the purposes of the invention comprise numerous individual units in which at least one active ingredient particle, preferably a plurality of active ingredient particles, is present in a matrix composed of a mixture comprising at least one solid paraffin and one or more substances from the group of fatty alcohol, triglyceride and fatty acid ester. A plurality of active ingredient particles is preferably present i) in a matrix composed of a mixture comprising at least one fatty alcohol and at least one solid paraffin, ii) in a matrix composed of a mixture of at least one triglyceride and at least one solid paraffin or iii) in a matrix composed of a mixture of at least one fatty acid ester and at least one solid paraffin. The active ingredient is preferably present in essentially uniform distribution, in particular in the homogeneous dispersion or solution, in the matrix. The active ingredient units are preferably microspheres.

The active ingredient units of the invention are distinguished in particular by high stability, an active ingredient release which can be controlled via the particle size and composition of the matrix, good flow characteristics, good compressibility and a uniform delivery of active ingredient. It is particularly worthy of mention that the active ingredient units of the invention can be further processed to a large number of pharmaceutical dosage forms without thereby losing a given functionality (such as taste masking, resistance to gastric juice, slowing of release). Thus, for example, on compression of the active ingredient units of the invention, no loss of functionality is observed even if there is deformation of the active ingredient units, which occurs in some circumstances. In contrast to this, with conventional pellets having a functional coating (such as taste masking, resistance to gastric juice, slowing of release) there is observed to be on further processing to dosage forms, for example on compression to tablets, a certain degree of damage to the coating and thus to the functionality. This may also lead to unwanted release of active ingredient in some cases.

The particle size of the individual units is advantageously less than or equal to 2 mm, preferably 50–800 µm, particularly preferably 50–700 µm and very particularly preferably 50–600 µm. Microspheres with a particle size of 50–500 µm, particularly preferably of 50–400 µm, are preferred. Monomodal microspheres with a particle size of 50–400 µm, particularly preferably of 50–200 µm, are particularly preferred.

Examples of acid-labile active ingredients in the sense of the present invention are acid-labile proton pump inhibitors.

Acid-labile proton pump inhibitors ($H^+/K^+$-APTase inhibitors) in the sense of the present invention which should be particularly mentioned are substituted pyridin-2-ylmethylsulfinyl-1H-benzimidazoles like those disclosed, for example, in EP-A-0 005 129, EP-A-0 166 287, EP-A-0 174 726, EP-A-0 184 322, EP-A-0 261 478 and EP-A-0 268 956. Those which may be mentioned as preferred in this connection are 5-methoxy-2-[(4-methoxy-3,5-dimethyl-2-pyridinyl)methylsulfinyl)-1H-benzimidazole (INN: omeprazole), 5-difluoromethoxy-2-[(3,4-dimethoxy-2-pyridinyl)methylsulfinyl]-1H-benzimidazole (INN: pantoprazole), 2-[3-methyl-4-(2,2,2-trifluoroethoxy)-2-pyridinyl)methylsulfinyl)-1H-benzimidazole (INN: lansoprazole) and 2-{[4-(3-methoxypropoxy)-3-methylpyridin-2-yl]methylsulfinyl)-1H-benzimidazole (INN: rabeprazole).

Further acid-labile proton pump inhibitors, for example substituted phenylmethylsulfinyl-1H-benzimidazoles, cycloheptapyridin-9-ylsulfinyl-1H-benzimidazoles or pyridin-2-ylmethylsulfinylthienoimidazoles are disclosed in DE-A 35 31 487, EP-A-0 434 999 and EP-A-0 234 485. Examples which may be mentioned are 2-[2-(N-isobutyl-N-methylamino)benzylsulfinyl]benzimidazole (INN: leminoprazole) and 2-(4-methoxy-6,7,8,9-tetrahydro-5H-cyclohepta[b]pyridin-9-ylsulfinyl)-1H-benzimidazol (INN: nepaprazole).

The acid-labile proton pump inhibitors are chiral compounds. The term "acid-labile proton pump inhibitor" also encompasses the pure enantiomers of the acid-labile proton pump inhibitors and their mixtures in any mixing ratio. Pure enantiomers which may be mentioned by way of example are 5-methoxy-2-[(S)-[(4-methoxy-3,5-dimethyl-2-pyridinyl)methyl]sulfinyl]-1H-benzimidazole (INN: esome prazole) and (−)-pantoprazole.

The acid-labile proton pump inhibitors are moreover present as such or, preferably, in the form of their salts with bases. Examples of salts with bases which may be mentioned are sodium, potassium, magnesium or calcium salts. If the acid-labile proton pump inhibitors are isolated in crystalline form, they may contain variable amounts of solvent. The term acid-labile proton pump inhibitor therefore also represents according to the invention all solvates, in particular all hydrates, of the acid-labile proton pump inhibitors and their salts. Such a hydrate of the salt of an acid-labile proton pump inhibitor with a base is disclosed, for example, in WO91/19710.

Acid-labile proton pump inhibitors which may be mentioned as particularly preferred are pantoprazole sodium sesquihydrate (=pantoprazole sodium×1.5 $H_2O$), (−)-pantoprazole sodium sesquihydrate, Pantoprazole magnesium dehydrate, omeprazole magnesium, omeprazole and esomeprazole.

The fatty alcohol is preferably a linear, saturated or unsaturated primary alcohol with 10–30 carbon atoms. It is preferably a primary alcohol with 10 to 18 carbon atoms in linear chains. Examples of fatty alcohols which may be mentioned are cetyl alcohol, myristyl alcohol, lauryl alcohol or stearyl alcohol, with preference for cetyl alcohol. It is also possible if desired for mixtures of fatty alcohols to be present.

The triglyceride is glycerol with its three hydroxyl groups esterified by carboxylic acids. The carboxylic acids are preferably monobasic carboxylic acids with 8 to 22 carbon atoms, preferably naturally occurring carboxylic acids. It is possible in this case for the carboxylic acids to be different or, preferably, identical. Examples which may be mentioned are tristearate, tripalmitate and, particularly preferably, trimyristate (these triglycerides are commercially available under the name Dynasan 118, 116 and 114 respectively). It is also possible if desired for mixtures of triglycerides to be present.

The fatty acid ester is the ester of an alcohol with a fatty acid. The alcohol in this case is preferably a linear, saturated or unsaturated primary alcohol with 10–30, preferably with 12 to 18, carbon atoms. The fatty acid is preferably a monobasic carboxylic acid with 8 to 22, in particular 12 to 18, carbon atoms, preferably a naturally occurring carboxylic acid. Fatty acid esters preferred according to the invention have a melting point above 30° C. Examples of fatty acid esters which may be mentioned are cetyl palmitate, which is commercially available for example under the name Cutina® CP. It is also possible if desired for mixtures of fatty acid esters to be present.

The solid paraffin is preferably paraffinum solidum (ceresin). It is also possible alternatively to use ozokerite, for example. It is also possible if desired to use mixtures.

If desired, the mixtures in the individual active ingredient units may include one or more other pharmaceutically suitable excipients. Other suitable excipients which may be mentioned by way of example are polymers, sterols and basic compounds.

Examples of polymers which may be mentioned are povidone (e.g. Kollidon® 17, 30 and 90 from BASF), vinylpyrrolidone/vinyl acetate copolymer and polyvinyl acetate. Others which may be mentioned are cellulose ethers [such as, for example, methylcellulose, ethylcellulose (Ethocel®) and hydroxypropylmethylcellulose], cellulose esters [such as cellulose acetate phthalate (CAP), cellulose acetate trimellitate (CAT), hydroxypropylmethylcellulose phthalate (HP50 and HP55) or hydroxypropylmethylcellulose acetate succinate (HPMCAS)], methacrylic acid/methyl methacrylate copolymer or methacrylic acid/ethyl methacrylate copolymer (Eudragit® L). The polymer is preferably povidone or ethylcellulose. It is also possible if desired for mixtures of polymers to be present. It is possible by adding suitable polymers, for example, to influence the pharmaceutical properties of the individual active ingredient units (e.g. delivery of the active ingredient).

The sterol is preferably a phytosterol or a zoosterol. Examples of phytosterols which may be mentioned are ergosterol, stigmasterol, sitosterol, brassicasterol and campesterol. Examples of zoosterols which may be mentioned are cholesterol and lanosterol. It is also possible if desired for mixtures of sterols to be present.

Examples of suitable basic compounds are inorganic basic salts such as ammonium carbonate and sodium carbonate, amines such as meglumine, di-, triethylamine and TRIS(2-amino-2-hydroxymethyl-1,3-propanediol) or fatty amines such as stearylamine. Stearylamine may be mentioned as preferred. The addition of basic compounds to the mixtures in the individual units results in particularly stable preparations and prevents possible discolorations.

The proportion (in percent by weight) of active ingredient in the individual active ingredient unit is advantageously 1–90%. The proportion of active ingredient is preferably 2–70%, particularly preferably 5–40%, in particular 10–20%. The proportion of fatty alcohol in the individual active ingredient unit is advantageously 10–70%, preferably 20–70%, particularly preferably 20–60% and in particular 30–60% The proportion of triglyceride in the individual active ingredient unit is advantageously 10–70%, preferably 20–70%, particularly preferably 20–60% and in particular 30–60%. The proportion of fatty acid ester in the individual active ingredient unit is advantageously 10–70%, preferably 20–70%, particularly preferably 20–60% and in particular 30–60%. The proportion of solid paraffin is advantageously 10–70%, preferably 20–60% and in particular 30–60%. If present, the proportion of polymer in the individual active ingredient unit is expediently 1–25%, preferably 1–10%, particularly preferably 5–10%. If present, the proportion of sterol is expediently 1–10%, preferably 1–5%. If present, the proportion of basic compound is 0.05–5%, preferably 0.1–1%.

Preferred individual active ingredient units of the invention consist of 2–70% active ingredient, 10–60% fatty alcohol, 10–60% solid paraffin, 1–15% polymer and 0.1–2% of a basic compound. Further particularly preferred individual active ingredient units of the invention consist of 2–70% active ingredient, 10–60% triglyceride, 10–60% solid paraffin, 1–15% polymer and 0.1–2% of a basic compound. Other particularly preferred individual active ingredient units of the invention consist of 2–70% active ingredient, 10–60% fatty acid ester, 10–60% solid paraffin, 1–15% polymer and 0.1–2% of a basic compound.

Particularly preferred individual active ingredient units of the invention consist of 5–40% active ingredient, 20–60% fatty alcohol, 10–60% solid paraffin, 1–15% polymer and 0.1–1% of a basic compound. Further particularly preferred individual active ingredient units of the invention consist of 5–40% active ingredient, 20–60% triglyceride, 10–60% solid paraffin, 1–15% polymer and 0.1–1% of a basic compound. Other particularly preferred individual active ingredient units of the invention consist of 5–40% active ingredient, 20–60% fatty acid ester, 10–60% solid paraffin, 1–15% polymer and 0.1–1% of a basic compound.

Examples of active ingredient units of the invention contain 5–40% pantoprazole sodium sesquihydrate, 10–40% cetyl alcohol, 5–60% solid paraffin, 1–5% polymer and 0.1–0.2% of a basic compound. Further examples of active ingredient units of the invention contain 5–40% pantoprazole sodium sesquihydrate, 10–40% glyceryl tripalmitate, 5–60% solid paraffin, 1–5% polymer and 0.1–0.2% of a basic compound. Other examples of active ingredient units of the invention contain 5–40% pantoprazole sodium sesquihydrate, 10–40% glyceryl tripalmitate, 5–60% solid paraffin, 1–5% polymer and 0.1–0.2% of a basic compound. Still other examples of active ingredient units of the invention contain 10–20% pantoprazole sodium sesquihydrate, 20–40% triglyceride, 40–70% solid paraffin, 1–5% sterol and 0.05–0.1% of a basic compound.

The individual active ingredient units can be produced for example by spray drying or, preferably, by spray solidification, in particular also by spray prilling. Production is particularly preferably by prilling, in particular by vibration prilling.

For the spray solidification or prilling expediently the fatty alcohol, the triglyceride and/or the fatty acid ester is liquefied together with the solid paraffin and, if desired, other excipients to give a clear melt. The active ingredient is dissolved or dispersed in this solution, and the resulting solution or dispersion is sprayed or, preferably, prilled in a suitable apparatus. A dispersion of the active ingredient in a melt of the excipients is preferably used.

Spray solidification takes place in a manner known per se. A detailed description of this technique is to be found in P. B. Deasy, Microencapsulation and Related Drug Processes (1984).

The individual active ingredient units are particularly preferably produced by solidification from liquid phase by generating drops by means of vibrating nozzles and by solidifying the drops which are formed, after they have stabilized, by drying or cooling in a suitable medium (preferably gaseous or liquid). The suitable medium may be, for example, cooled gas such as air or nitrogen. Processes of this type and corresponding apparatuses are disclosed in DE 27 25 924, EP 0 467 221, WO99/33555 and WO00/24382. It is particularly preferred in this connection for the liquid phase flowing to the nozzle to be kept at a constant temperature. The solidification preferably takes place by instantaneous cooling in a suitable cooling medium. In prilling, moreover it is preferred for the liquid phase flowing to the nozzle, the vibrating nozzle and the drops formed by prilling to be kept at a constant temperature until their spherical shape has stabilized, and for the solidification of the drops after their stabilization to be carried out instantaneously by cooling with a gaseous or liquid cooling medium. Systems suitable for prilling by means of vibrating nozzles are marketed, for example, by Brace GmbH, Alzenau, Germany. It is possible by means of prilling using vibrating nozzles to obtain the individual active ingredient units in the form of microspheres with a narrow monomodal particle size spectrum in the particle size range from 50 µm to 2 mm. The narrow monomodal particle size spectrum and the uniform spherical shape of the microspheres obtained in this way are expected to result in a uniformly smooth surface, a uniform, defined delivery of active ingredient and, in relation to passage through the stomach in the case of oral dosage forms (owing to the small particles), a behavior like that of a solution. The microspheres of the invention distinguished in particular by high stability, a release of active ingredient which can be controlled via the particle size and composition of the matrix, good flow characteristics, good compressibility and a uniform delivery of active ingredient. It is particularly worthy of mention that the microspheres can be further processed to a large number of pharmaceutical dosage forms without thereby losing a given functionality (such as taste masking, resistance to gastric juice, slowing of release). Thus, for example, on compression of the microspheres of the invention to the rapidly disintegrating tablet of the invention there is observed to be no loss of functionality, in particular of acid resistance. Compression of pellets with an enteric coating to tablets may on the other hand, as described at the outset, be difficult because there is always the risk that the compression is associated with damage to the coating and thus to the functionality, thus leading to an unwanted release or decomposition of the active ingredient.

The microspheres are preferably monomodal microspheres with a particle size range of 50–800 µm, preferably 50–500 µm, particularly preferably 50–400 µm, in particular 50–200 µm. The microspheres preferably comprise an acid-labile proton pump inhibitor.

The particle size of the active ingredient employed in the spray drying or spray solidification, prilling or vibration prilling is advantageously less than or equal to 100 µm, in particular less than 40 µm. The particle size is preferably in the range 1–20 µm, particularly preferably in the range 3–15 µm. Such a particle size can be achieved, for example, by grinding the active ingredient in a suitable mill.

The individual active ingredient units (preparations) of the invention can then be further processed together with excipients which bring about rapid disintegration of the tablet on oral intake to give the dosage form of the invention. Suitable excipients are, in particular, those excipients which on oral intake of the tablet bring about rapid disintegration of the tablet. Excipients which on oral intake of the tablet bring about rapid disintegration of the tablet preferably comprise one or more substances selected from the group of fillers and disintegrants. One or more other excipients from the group of lubricants, flavors, flavoring substances and surface-active substances are preferably present in the rapidly disintegrating dosage form of the invention. Binders can also be present if desired. The rapidly disintegrating dosage form particularly preferably comprises a mixture of at least one filler, one disintegrant and one lubricant. Fillers suitable according to the invention are, in particular, basic fillers such as calcium carbonate (e.g. MagGran® CC or Destab® 95) and sodium carbonate, sugar alcohols such as mannitol (e.g. Perlitol® or Parteck® M), sorbitol (e.g. Karion®), xylitol or maltitol, starches such as corn starch, potato starch and wheat starch, microcrystalline cellulose, saccharides such as glucose, lactose, levulose, sucrose and dextrose. In a preferred embodiment of the invention the rapidly disintegrating dosage form comprises a basic filler such as sodium carbonate or calcium carbonate. In a further preferred development of the invention, the rapidly disintegrating dosage form of the invention comprises as filler a mixture of a basic filler (in particular calcium carbonate) and a sugar alcohol (in particular sorbitol or mannitol). Disintegrants suitable according to the invention are, in particular, insoluble polyvinylpyrrolidone (insoluble PVP, crospovidone), sodium carboxy-methylstarch, sodium carboxymethylcellulose, alginic acid and starches able to carry out the function of a disintegrant (e.g. Starch 1500). Suitable lubricants which may be mentioned are sodium stearyl fumarate, magnesium stearate, calcium stearate, stearic acid, talc and highly disperse silica (Aerosil). Suitable surface-active substances which may be mentioned are sodium lauryl sulfate or Tween® 20, 60 or 80. Binders suitable according to the invention are polyvinylpyrrolidone (PVP, Polyvidon® K25, 90) or mixtures of PVP with polyvinyl acetate (e.g. Kollidon® 64), gelatin, cornstarch mucilage, preswollen starches (Starch 1500), hydroxypropylmethylcellulose (HPMC) or hydroxypropylcellulose (L-HPC).

In another embodiment of the invention the rapidly disintegrating tablet contains one or more basic (alkaline) additives in particular additives which are known to have antacid activity in the treatment of gastrointestinal disorders associated with excess gastric acid excretion. Examples of such basic additives having antacid activity which may be mentioned in connection with the invention are alkaline buffer compounds such as trisodium phosphate, disodium phosphate, phosphates such as aluminium phosphate, hydroxides such as magnesium hydroxide, aluminium hydroxide, aluminium-sodium-carbonate-dihydroxide, oxides, such as aluminium oxide or magnesium oxide, carbonates such as sodium carbonate, magnesium carbonate, calcium carbonate, potassium carbonate, hydrogen carbonates such as sodium hydrogen carbonate, potassium hydrogen carbonate, alkaline amino acids or alkaline salts of amino acids such as sodium glycine or suitable salts of fatty acids such as potassium oleate, ammonium oleate or salts of bismuth such as alkaline bismuth nitrate, bismuth gallate, or silicats such as aluminium-magnesium-silicate, magnesium-trisilicate, or magaldrate or meglumine (USP 24) or trometamol (Ph.Eur.) or hydrotalcite. In a preferred embodiment of the invention the basic additive is a basic filler. For rapidly disintegrating tablets according to the invention which contain one or more basic (alkaline) additives with antacid activity surprisingly a rapid onset of action and a shortening of duration of treatment is observed in the treatment of gastrointestinal disorders associated with excess acid excretion.

The proportion (in percent by weight based on the finished tablet) of filler in the rapidly disintegrating tablet is advantageously from 1 to 99% by weight. The proportion of filler is preferably from 30 to 95% by weight, and the proportion is very particularly preferably from 60 to 85% by weight.

The proportion (in percent by weight based on the finished tablet) of disintegrant in the rapidly disintegrating tablet is usually from 1 to 30% by weight. The proportion of disintegrant is preferably from 2 to 15% by weight. The proportion of disintegrant is particularly preferably from 5 to 10% by weight.

The proportion (in percent by weight based on the finished tablet) of lubricant in the rapidly disintegrating tablet is usually from 0.1 to 5% by weight. The proportion of lubricant is preferably from 0.3 to 3% by weight. The proportion of lubricant is particularly preferably from 0.5 to 2% by weight.

The proportion (in percent by weight based on the finished tablet) of individual active ingredient units in the rapidly disintegrating tablet is usually from 1 to 90% by weight. The proportion of individual active ingredient units is preferably up to 70% by weight, in particular from 10 to 50% by weight. The proportion is very particularly preferably from 15 to 25% by weight.

The proportion (in percent by weight based on the finished tablet) of binder can be up to 10% by weight, and it can preferably be up to 5% by weight.

Preferably the basic additive is present in an amount sufficient to cause a rapid onset of action in the treatment of gastrointestinal disorders associated with excess gastric acid excretion. The proportion (in percent by weight based on the finished tablet) of basic additive is preferably from 0.5 to 80% by weight. It is particularly preferred that the amount of basic additive in the rapidly disintegrating tablet is from 3 to 30% by weight.

If desired, one or more flavoring substances (e.g. flavors or sweeteners) can additionally be present in the rapidly disintegrating tablet. This makes it possible, for example, to achieve an improvement of the taste of the rapidly disintegrating tablet. These substances are added in conventional amounts.

The rapidly disintegrating tablet is produced by processes known to the skilled worker. The rapidly disintegrating tablet is preferably produced by i) dry mixing of filler and/or disintegrant;
ii) production of granules of filler and binder and mixing of the granules with a disintegrant or
iii) dry granulation (briqueting or compacting) of one or more excipient components.

The individual active ingredient units are subsequently admixed to the mixtures obtained in i), ii) or iii) and then, if desired, flavors/flavoring substances and finally also one or more lubricants are admixed. The mixture obtained in this way can be compressed in a tablet press under conventional conditions.

Rapid disintegration of the tablet means according to the invention disintegration of the tablet in about 60 seconds or less when the tablet is subjected to a disintegration test as described in the European Pharmacopoeia (3rd edition, 1997) 2.9.1 disintegration time of tablets and capsules.

The rapidly disintegrating tablets of the invention comprise the acid-labile active ingredient in the dose customary for the treatment of the particular disorder. The acid-labile proton pump inhibitors of the invention can be employed for the treatment and prevention of all disorders which are regarded as treatable or preventable by the use of pyridin-2-ylmethylsulfinyl-1H-benzimidazoles. In particular, the rapidly disintegrating tablets of the invention can be employed for the treatment of gastric disorders. Such rapidly disintegrating tablets contain between 1 and 500 mg, preferably between 5 and 60 mg, of an acid-labile proton pump inhibitor. Examples which may be mentioned are tablets which contain 10, 20, 40 or 50 mg of pantoprazole. The daily dose (e.g. 40 mg of active ingredient) can be administered, for example, in the form of a single dose or by means of a plurality of doses of the tablets of the invention (e.g. 2×20 mg of active ingredient).

The tablets of the invention can be combined with other medicaments, either in different combinations or in a fixed combination. Combinations worthy of mention in connection with the dosage forms of the invention which comprise acid-labile proton pump inhibitors as active ingredients are those with anti-microbial active ingredients and combinations with NSAIDs (nonsteroidal anti-inflammatory drugs). Particular mention should be made of the combination with antimicrobial agents like those employed for controlling the microbe *Helicobacter pylori* (*H. pylori*).

Examples of suitable antimicrobial active ingredients (active against *Helicobacter pylori*) are described In EP-A-0 282 131. Examples of antimicrobial agents which are suitable for controlling the microbe *Helicobacter pylori* and may be mentioned by way of example are bismuth salts [e.g. bismuth subcitrate, bismuth subsalicylate, ammonium bismuth(III) potassium citrate dihydroxide, bismuth nitrate oxide, dibismuth tris(tetraoxodialuminate)], but especially β-lactam antibiotics, for example penicillins (such as benzylpenicillin, phenoxymethylpenicillin, propicillin, azidocillin, dicloxacillin, flucloxacillin, oxacillin, amoxicillin, bacampicillin, ampicillin, mezlocllin, piperacillin or aziocillin), cephalosporins (such as cefadroxil, cefaclor, cefalexin, cefixime, cefuroxime, cefetamet, ceftibuten, cefpodoxime, cefotetan, cefazoline, cefoperazone, ceftizoxime, cefotaxime, ceftazidime, cefamandole, cefepime, cefoxitin, cefodizime, cefsulodin, ceftriaxone, cefotiam or cefmenoxime) or other β-lactam antibiotics (e.g. aztreonam, loracarbef or meropenem); enzyme inhibitors, for example sulbactam; tetracyclines, for example tetracycline, oxytetracycline, minocycline or doxycycline; aminoglycosides, for example tobramycin, gentamicin, neomycin, streptomycin, amikacin, netilmicin, paromomycin or spectinomycin; amphenicols, for example chloramphenicol or thiamphenicol; lincomycins and macrolide antibiotics, for example clindamycin, lincomycin, erythromycin, clarithromycin, spiramycin, roxithromycin or azithromycin; polypeptide antibiotics, for example colistin, polymixin B, teicoplanin or vancomycin; gyrase inhibitors, for example norfloxacin, cinoxacin, ciprofloxacin, pipemidic acid, enoxacin, nalidixic acid, pefloxacin, fleroxacin or ofloxacin; nitroimidazoles, for example metronidazole; or other antibiotics, for example fosfomycin or fusidic acid. Particularly worthy of mention in this connection is the administration of an acid-labile proton pump inhibitor together with the combination of a plurality of antimicrobial active ingredients, for example with the combination of a bismuth salt and/or tetracycline with metronidazole or the combination of amoxicillin or clarithromycin with metronidazole and amoxicillin with clarithromycin.

The production of tablets and preparations of the invention is described by way of example hereinafter. The following examples explain the invention in detail without restricting it.

EXAMPLES

Production of the Active Ingredient Units

Example 1

50 g of solid paraffin, 34.9 g of cetyl alcohol and 0.1 g of stearylamine are converted into a clear melt. 5.0 g of povidone is dissolved in the clear melt. At a temperature between 56–60° C., 10.0 g of pantoprazole sodium sesquihydrate is added and suspended homogeneously. The suspension is prilled in the molten state, and the drops thus produced are solidified in a cooling zone.

Example 2

55 g of solid paraffin, 30.9 g of cetyl alcohol and 0.1 g of stearylamine are converted into a clear melt. 4.0 g of povidone is dissolved in the clear melt. At a temperature between 56–60° C., 10.0 g of pantoprazole magnesium is added and suspended homogeneously. The suspension is prilled in the molten state, and the drops thus produced are solidified in a cooling zone.

Example 3

45.0 g of solid paraffin, 33.8 g of cetyl alcohol, 1.0 g of β-sitosterol and 0.2 g of stearylamine are converted into a clear melt. 1.0 g of povidone and 4.0 g of ethylcellulose are dissolved in the clear melt. At a temperature between 56–60° C., 15.0 g of pantoprazole sodium sesquihydrate is added and suspended homogeneously. The suspension is prilled in the molten state, and the drops thus produced are solidified in a cooling zone.

Example 4

52.0 g of solid paraffin, 30.3 g of cetyl alcohol and 0.2 g of stearylamine are converted into a clear melt. 5.0 g of povidone is dissolved in the clear melt. At a temperature between 56–60° C., 12.5 g of pantoprazole sodium sesquihydrate is added and suspended homogeneously. The suspension is prilled in the molten state, and the drops thus produced are solidified in a cooling zone.

Example 5

77.2 g of cetyl alcohol and 0.3 g of stearylamine are converted into a clear melt. 10.0 g of povidone is dissolved in the clear melt. At a temperature between 56–60° C., 12.5 g of pantoprazole sodium sesquihydrate is added and suspended homogeneously. The suspension is prilled in the molten state, and the drops thus produced are solidified in a cooling zone.

Example 6

47 g of solid paraffin, 40 g of glyceryltripalmitate (Dynasan 116, from Hüls) and 3 g of sitosterol are converted into a clear melt at 100° C. and cooled to 55–60° C. 10 g of lansoprazole are added and suspended homogeneously. The suspension is put in the feed container of a prilling unit (from Brace) and prilled from a 200 μm nozzle at about 0.1 bar. A periodic vibration with a frequency of about 390 Hz is transmitted to the nozzle head during this. The resulting drops are solidified in a cooling zone with air at a temperature of −30° C.

Example 7

15 g of glyceryl trimyristate (Dynasan 114), 15 grams of glyceryl tripalmitate (Dynasan 116), 50 grams of solid paraffin and 5 g of cholesterol are converted into a clear melt at about 100° C. The clear melt is cooled to about 55–65° C. 15 g of rabeprazole are added, the active ingredient is uniformly dispersed, and the homogeneous suspension is prilled as in example 6.

Example 8

10 g of glyceryl tripalmitate (Dynasan 116), 20 g of glyceryl trimyristate (Dynasan 114), 52 g of solid paraffin and 3 g of sitosterol are converted into a clear melt at about 100° C. The clear melt is cooled to 55–65° C. 15 g of omeprazole Mg are added and suspended homogeneously. The suspension is put in the feed container of a prilling unit (from Brace) and prilled through a 200 μm nozzle at 90 mbar. A periodic vibration with a frequency of about 400 Hz is transmitted to the nozzle head during this. The resulting drops are solidified with air at a temperature of −30° C. in a cooling zone.

Example 9

18 g of tristearin, 60 g of solid paraffin and 5 g of cholesterol are converted into a clear melt. The clear melt is cooled to 56–60° C. 10 g of pantoprazole sodium sesquihydrate are introduced and homogeneously dispersed. The suspension is prilled in the molten state in a prilling unit (from Brace) with vibrating nozzles, and the resulting drops are solidified in a cooling zone.

Example 10

18 g of cetyl palmitate, 40 g of solid paraffin and 2 g of cholesterol are converted into a clear melt. The clear melt is cooled to 56–60° C. 10 g of pantoprazole sodium sesquihydrate are introduced and homogenized until a uniform suspension results. The suspension is prilled in the molten state in a prilling unit (from Brace) with vibrating nozzles, and the resulting drops are solidified in a cooling zone.

Example 11

50 g of solid paraffin and 40 g of cetyl palmitate (Cutina® CP) are converted into a clear melt at 100° C. The clear melt is cooled to 50–60° C. 10 g of pantoprazole sodium sesquihydrate are introduced and suspended homogeneously. The suspension is prilled in the molten state in a prilling unit (from Brace) with vibrating nozzles (200 μm nozzle), and the resulting drops are solidified in a cooling zone.

Example 12

50 g of solid paraffin and 40 g of cetyl alcohol are converted into a clear melt at 100° C. The clear melt is cooled to 50–60° C. 10 g of pantoprazole sodium sesquihydrate are introduced and suspended homogeneously. The suspension is prilled in the molten state in a prilling unit (from Brace) with vibrating nozzles (200 μm nozzle), and the resulting drops are solidified in a cooling zone.

Example 13

50 g of solid paraffin and 40 g of glyceryl trimyristate are converted into a clear melt at 100° C. The clear melt is cooled to 50–60° C. 10 g of pantoprazole sodium sesquihydrate are introduced and suspended homogeneously. The suspension is prilled in the molten state in a prilling unit (from Brace) with vibrating nozzles (200 µm nozzle), and the resulting drops are solidified in a cooling zone.

Example 14

47 g of solid paraffin, 40 g of glyceryl tripalmitate (Dynasan 116, from Hüls) and 3 g of sitosterol are converted into a clear melt at 100° C. and cooled to 50–60° C. 10 g of lansoprazole are added and suspended homogeneously. The suspension is put into the feed container of a prilling unit (from Brace) and prilled from a 200 µm nozzle at about 0.1 bar. A periodic vibration with a frequency of about 390 Hz is transmitted to the nozzle head during this. The resulting drops are solidified in a cooling zone with air at a temperature of −30° C.

Example 15

30 g of tristearin, 60 g of solid paraffin and 4 g of sitosterol and 0.07 g stearylamine are converted into a clear melt. The clear melt is cooled to 56–60° C., 15 g of pantoprazole sodium sesquihydrate are introduced and homogeneously dispersed. The suspension is prilled in the molten state in a prilling unit (from Brace) with vibrating nozzles, and the resulting drops are solidified in a cooling zone.

Example 16

17.5 g of glyceryl trimyristate (Dynasan 114), 67.5 g of solid paraffin and 5 g of cholesterol are converted into a clear melt at about 100° C. The clear melt is cooled to about 55–65° C. 10 g of pantoprazole are added, and the active ingredient is uniformly dispersed, and the homogeneous suspension is prilled as in example 6.

Example 17

56.7 g of cetyl alcohol, 3 g of vinylpyrollidone/vinyl acetate copolymer, 15 g of solid paraffin, 15 g of cetyl palmitate and 0.1 g of sodium stearate are converted into a clear melt. At a temperature between 56–60° C., 10.0 g of pantoprazole sodium sesquihydrate is added and suspended homogeneously. The suspension is prilled in the molten state at 60° C. and the drops thus produced are solidified in a cooling zone.

Example 18

46.7 g of cetostearylic alcohol, 4 g of vinylpyrollidone/vinyl acetate copolymer, 23 g solid paraffin, 0.3 g of sodium stearate and 1 g sitosterol are converted into a clear melt. At a temperature between 60–65° C., 10.0 g of pantoprazole sodium sesquihydrate is added and suspended homogeneously. The suspension is prilled in the molten state at 60 to 65° C. and the drops thus produced are solidified in a cooling zone.

Example 19

39.9 g of cetyl alcohol, 3 g of vinylpyrollidone/vinyl acetate copolymer, 20 g of cetyl palmitate, 2 g cholesterol, 17 g solid paraffin and 0.1 g of sodium stearate are converted into a clear melt. At a temperature between 56–60° C., 18.0 g of pantoprazole sodium sesquihydrate is added and suspended homogeneously. The suspension is prilled in the molten state at 60° C. and the drops thus produced are solidified in a cooling zone.

Example 20

47.9 g cetostearylic alcohol, 2 g of vinylpyrollidone/vinyl acetate copolymer, 25 g of cetyl palmitate, 1 g sitosterol, 15 g solid paraffin and 0.1 g of sodium stearate are converted into a clear melt. At a temperature between 56–60° C., 15.0 g of pantoprazole sodium sesquihydrate is added and suspended homogeneously. The suspension is prilled in the molten state at 60° C. and the drops thus produced are solidified in a cooling zone.

The preparations obtained as in examples 1–20 have a particle size in the range 50–700 µm. It is possible, for example by varying the process conditions, to obtain larger particles.

Production of Rapidly Disintegrating Tablets

Example A

| | | |
|---|---|---|
| 1. | MagGran ® CC | 1008.0 mg |
| 2. | Karion ® | 432.0 mg |
| 3. | Crospovidone | 136.0 mg |
| 4. | Preparation from example 1 | 400.0 mg |
| 5. | Magnesium stearate | 24.0 mg |
| | Total | 2000.0 mg |

Production: 1.–4. are mixed in a free-fall mixer. Then 5. is added through a suitable sieve to the mixture of 1.–4., followed by a brief mixing once again. The mixture obtained in this way is compressed in a tablet press.

Example B

| | | |
|---|---|---|
| 1. | Destab ® 95 SE | 1060.8 mg |
| 2. | Pearlitol ® 300 DC | 387.2 mg |
| 3. | Crospovidone | 136.0 mg |
| 4. | Preparation from example 16 | 400.0 mg |
| 5. | Magnesium stearate | 16.0 mg |
| | Total | 2000.0 mg |

Production: 1.–4. are mixed in a free-fall mixer. Then 5. is added through a suitable sieve to the mixture of 1.–4., followed by a brief mixing once again. The mixture obtained in this way is compressed in a tablet press.

Example C

| | | |
|---|---|---|
| 1. | Destab ® 95 SE | 1072.0 mg |
| 2. | Pearlitol ® 300 DC | 432.0 mg |
| 3. | Crospovidone | 80.0 mg |
| 4. | Preparation from example 3 | 400.0 mg |
| 5. | Magnesium stearate | 16.0 mg |
| | Total | 2000.0 mg |

Production: 1.–4. are mixed in a free-fall mixer. Then 5. is added through a suitable sieve to the mixture of 1.–4., followed by a brief mixing once again. The mixture obtained in this way is compressed in a tablet press.

Example D

| | | |
|---|---|---|
| 1. | MagGran ® CC | 1008.0 mg |
| 2. | Karion ® | 432.0 mg |
| 3. | Sodium carboxymethylcellulose | 136.0 mg |
| 4. | Preparation from example 8 | 266.6 mg |
| 5. | Magnesium stearate | 24.0 mg |
| | Total | 1866.6 mg |

Production: 1.–4. are mixed in a free-fall mixer. Then 5. is added through a suitable sieve to the mixture of 1.–4., followed by a brief mixing once again. The mixture obtained in this way is compressed in a tablet press.

Example E

| | | |
|---|---|---|
| 1. | Lactose 1-hydrate | 1136.0 mg |
| 2. | Corn starch | 288.0 mg |
| 3. | Polyvidon ® K 25 | 80.0 mg |
| 4. | Sodium carboxymethylstarch | 80.0 mg |
| 5. | Preparation from example 2 | 400.0 mg |
| 6. | Magnesium stearate | 16.0 mg |
| | Total | 2000.0 mg |

Production: 1. and 2. are granulated with a solution of 3. Drying and screening are carried out. 4. and 5. are admixed by means of a free fall mixer for several minutes, and then 6. is briefly admixed by means of a free fall mixer. The mixture obtained in this way is compressed in a tablet press.

Example F

| | | |
|---|---|---|
| 1. | Lactose 1-hydrate | 1136.0 mg |
| 2. | Corn starch | 288.0 mg |
| 3. | Polyvidon ® K 25 | 80.0 mg |
| 4. | Sodium carboxymethylcellulose | 80.0 mg |
| 5. | Preparation from example 16 | 400.0 mg |
| 6. | Magnesium stearate | 16.0 mg |
| | Total | 2000.0 mg |

Production: 1. and 2. are granulated with a solution of 3. Drying and screening are carried out. 4. and 5. are admixed by means of a free fall mixer for several minutes, and then 6. is briefly admixed by means of a free fall mixer. The mixture obtained in this way is compressed in a tablet press.

Example G

| | | |
|---|---|---|
| 1. | Lactose 1-hydrate | 1192.0 mg |
| 2. | Corn starch | 288.0 mg |
| 3. | Polyvidon ® K 90 | 24.0 mg |
| 4. | Crospovidone | 80.0 mg |
| 5. | Preparation from example 1 | 400.0 mg |
| 6. | Magnesium stearate | 16.0 mg |
| | Total | 2000.0 mg |

Production: 1. and 2. are granulated with a solution of 3. Drying and screening are carried out. 4. and 5. are admixed by means of a free fall mixer for several minutes, and then 6. is briefly admixed by means of a free fall mixer. The mixture obtained in this way is compressed in a tablet press.

Example H

| | | |
|---|---|---|
| 1. | MagGran ® CC | 1008.0 mg |
| 2. | Karion ® | 432.0 mg |
| 3. | Crospovidone | 136.0 mg |
| 4. | Preparation from example 1 | 400.0 mg |
| 5. | Microcrystalline cellulose | 400.0 mg |
| 6. | Magnesium stearate | 24.0 mg |
| | Total | 2400.0 mg |

Production: 1.–5. are mixed in a free-fall mixer. Then 6. is added through a suitable sieve to the mixture of 1.–5., followed by a brief mixing once again. The mixture obtained in this way is compressed in a tablet press.

Example I

| | | |
|---|---|---|
| 1. | Destab ® 95 SE | 1060.8 mg |
| 2. | Pearlitol ® 300 DC | 387.2 mg |
| 3. | Crospovidone | 136.0 mg |
| 4. | Preparation from example 16 | 400.0 mg |
| 5. | Microcrystalline cellulose | 400.0 mg |
| 6. | Magnesium stearate | 16.0 mg |
| | Total | 2400.0 mg |

Production: 1.–5. are mixed in a free-fall mixer. Then 6. is added through a suitable sieve to the mixture of 1.–5., followed by a brief mixing once again. The mixture obtained in this way is compressed in a tablet press.

Example J

| | | |
|---|---|---|
| 1. | Destab ® 95 SE | 1072.0 mg |
| 2. | Pearlitol ® 300 DC | 432.0 mg |
| 3. | Crospovidone | 80.0 mg |
| 4. | Preparation from example 3 | 400.0 mg |
| 5. | Microcrystalline cellulose | 400.0 mg |
| 6. | Magnesium stearate | 16.0 mg |
| | Total | 2400.0 mg |

Production: 1.–5. are mixed in a free-fall mixer. Then 6. is added through a suitable sieve to the mixture of 1.–5., followed by a brief mixing once again. The mixture obtained in this way is compressed in a tablet press.

Example K

| | | |
|---|---|---|
| 1. MagGran ® CC | 1008.0 | mg |
| 2. Karion ® | 432.0 | mg |
| 3. Sodium carboxymethylcellulose | 136.0 | mg |
| 4. Preparation from example 8 | 266.6 | mg |
| 5. Microcrystalline cellulose | 266.6 | mg |
| 6. Magnesium stearate | 24.0 | mg |
| Total | 2133.2 | mg |

Production: 1.–5. are mixed in a free-fall mixer. Then 6. is added through a suitable sieve to the mixture of 1.–5., followed by a brief mixing once again. The mixture obtained in this way is compressed in a tablet press.

Example L

| | | |
|---|---|---|
| 1. sodium carbonate anhydrous | 120.0 | mg |
| 2. Microcrystalline cellulose | 1360.0 | mg |
| 3. Sodium carboxymethylstarch | 100.0 | mg |
| 4. Preparation from example 18 | 400.0 | mg |
| 5. Magnesium stearate | 20.0 | mg |
| Total | 2000.0 | mg |

Production: 1.–4. are mixed in a free-fall mixer. Then 5. is added through a suitable sieve to the mixture of 1.–4., followed by a brief mixing once again. The mixture obtained in this way is compressed in a tablet press.

Example M

| | | |
|---|---|---|
| 1. Microcrystalline cellulose | 1480.0 | mg |
| 2. Sodium carboxymethylstarch | 100.0 | mg |
| 3. Preparation from example 19 | 400.0 | mg |
| 4. Magnesium stearate | 20.0 | mg |
| Total | 2000.0 | mg |

Production: 1.–3. are mixed in a free-fall mixer. Then 4. is added through a suitable sieve to the mixture of 1.–3., followed by a brief mixing once again. The mixture obtained in this way is compressed in a tablet press.

Example N

| | | |
|---|---|---|
| 1. Microcrystalline cellulose | 1480.0 | mg |
| 2. Preparation from example 20 | 400.0 | mg |
| 3. Magnesium stearate | 20.0 | mg |
| Total | 1900.0 | mg |

Production: 1. and 2. are mixed in a free-fall mixer. Then 3. is added through a suitable sieve to the mixture of 1.–2., followed by a brief mixing once again. The mixture obtained in this way is compressed in a tablet press.

Example O

| | | |
|---|---|---|
| 1. sodium carbonate anhydrous | 60.0 | mg |
| 2. Microcrystalline cellulose | 1340.0 | mg |
| 3. Sodium carboxymethylstarch | 50.0 | mg |
| 4. Polyvidon ® K 25 | 80.0 | mg |
| 5. Preparation from example 17 | 400.0 | mg |
| 6. Sodium carboxymethylstarch | 50.0 | mg |
| 7. Magnesium stearate | 20.0 | mg |
| Total | 2000.0 | mg |

Production: 1., 2. and 3. are granulated with a solution of 4. Drying and screening are carried out. 5. and 6. are admixed by means of a free fall mixer for several minutes, and then 7. is briefly admixed by means of a free fall mixer. The mixture obtained in this way is compressed in a tablet press.

Example P

| | | |
|---|---|---|
| 1. Microcrystalline cellulose | 1330.0 | mg |
| 3. Sodium carboxymethylstarch | 150.0 | mg |
| 4. HPMC 2910 | 80.0 | mg |
| 5. Preparation from example 1 | 400.0 | mg |
| 6. Sodium carboxymethylstarch | 50.0 | mg |
| 7. Magnesium stearate | 20.0 | mg |
| Total | 2000.0 | mg |

Production: 1. and 2. are granulated with a solution of 3. Drying and screening are carried out. 4. and 5. are admixed by means of a free fall mixer for several minutes, and then 6. is briefly admixed by means of a free fall mixer. The mixture obtained in this way is compressed in a tablet press.

The invention claimed is:

1. A rapidly disintegrating tablet for oral administration of an acid-labile active ingredient comprising a plurality of individual active ingredient units together with one or more pharmaceutical excipients, where the acid-labile active ingredient is present in the individual active ingredient units in a matrix composed of a mixture comprising at least one solid paraffin and one or more substances from the group of fatty alcohol, triglyceride and fatty acid ester, and where excipients which, on oral intake of the tablet, bring about rapid disintegration of the tablet are present, wherein said acid-labile active ingredient is a proton pump inhibitor, or a hydrate, solvate, salt, hydrate of a salt or solvate of a salt thereof.

2. A rapidly disintegrating tablet for oral administration of an acid-labile active ingredient comprising a plurality of individual active ingredient units together with one or more pharmaceutical excipients, where the acid-labile active ingredient is present in the individual active ingredient units i) in a matrix composed of a mixture comprising at least one fatty alcohol and at least one solid paraffin, ii) in a matrix composed of a mixture comprising at least one triglyceride and at least one solid paraffin or iii) in a matrix composed of a mixture comprising at least one fatty acid ester and at least one solid paraffin, and where excipients which, on oral intake of the tablet, bring about rapid disintegration of the tablet are present, wherein said acid-labile active ingredient is a proton pump inhibitor, or a hydrate, solvate, salt, hydrate of a salt or solvate of a salt thereof, and wherein the tablet disintegrates in about 60 seconds or less when the tablet is subjected to a disintegration test as described in European Pharmacopoeia, 3$^{rd}$ Edition, 1997, 2.9.1 disintegration time of tablets and capsules.

3. A tablet as claimed in claim 1, where the excipients which bring about rapid disintegration of the tablet comprise one or more substances selected from the group consisting of fillers and disintegrants.

4. A tablet as claimed in claim 3, where the filler comprises a mixture of a sugar alcohol and a basic filler.

5. A tablet as claimed in claim 3, where the excipients comprise a mixture of at least one filler, one disintegrant and one lubricant.

6. A tablet as claimed in claim 3, where one or more excipients selected from the group consisting of lubricants, flavors, flavoring substances and surface-active substances are additionally present.

7. A tablet as claimed in claim 1, wherein the individual active ingredient units are microspheres.

8. A tablet as claimed in claim 1, wherein the acid-labile active ingredient is selected from the group consisting of pantoprazole, a hydrate of pantoprazole, a solvate of pantoprazole, a salt of pantoprazole, a hydrate of a salt of pantoprazole or a solvate of a salt of pantoprazole.

9. A tablet as claimed in claim 1, which comprises a basic filler.

10. A tablet as claimed in claim 2, wherein the individual active ingredient units are microspheres.

11. A tablet as claimed in claim 4, wherein the basic filler is calcium carbonate.

12. A tablet as claimed in claim 2, wherein the acid-labile active ingredient is selected from the group consisting of pantoprazole, a hydrate of pantoprazole, a solvate of pantoprazole, a salt of pantoprazole, a hydrate of a salt of pantoprazole or a solvate of a salt of pantoprazole.

13. A tablet as claimed in claim 1, wherein the acid-labile active ingredient is selected from the group consisting of pantoprazole sodium sesquihydrate, (−)-pantoprazole magnesium dihydrate, omeprazole magnesium, omeprazole and esomeprazole.

14. A tablet as claimed in claim 2, wherein the acid-labile active ingredient is selected from the group consisting of pantoprazole sodium sesquihydrate, (−)-pantoprazole magnesium dihydrate, omeprazole magnesium, omeprazole and esomeprazole.

* * * * *

UNITED STATES PATENT AND TRADEMARK OFFICE
CERTIFICATE OF CORRECTION

PATENT NO.        : 7,147,869 B2
APPLICATION NO. : 10/433397
DATED             : December 12, 2006
INVENTOR(S)       : Dietrich et al.

It is certified that error appears in the above-identified patent and that said Letters Patent is hereby corrected as shown below:

Claim 2, Column 18, Line 63, Please delete " paraffir," and replace with -- paraffin, --

Claim 2, Column 18, Line 67, and Column 19, Lines 1-4,
Please delete " thereof, and wherein the tablet disintegrates in about 60 seconds or less when the tablet is subjected to a disintegration test as described in European Pharmacopoeia, 3$^{rd}$ Edition, 1997, 2.9.1 disintegration time of tablets and capsules. " and replace with -- thereof. --

Signed and Sealed this

Sixth Day of March, 2007

JON W. DUDAS
*Director of the United States Patent and Trademark Office*